United States Patent
Muggetti et al.

(10) Patent No.: US 6,730,664 B1
(45) Date of Patent: May 4, 2004

(54) FORMULATIONS FOR PARENTERAL USE OF ESTRAMUSTINE PHOSPHATE AND SULFOALKYL ETHER CYCLODEXTRINS

(75) Inventors: Lorena Muggetti, Meda (IT); Paolo Colombo, Milan (IT); Alessandro Martini, Milan (IT); Giovanni Buzzi, Milan (IT)

(73) Assignee: Pharmacia Italia S.p.A., Milan (IT)

( * ) Notice: Subject to any disclaimer, the term of this patent is extended or adjusted under 35 U.S.C. 154(b) by 26 days.

(21) Appl. No.: 10/070,416

(22) PCT Filed: Aug. 3, 2000

(86) PCT No.: PCT/EP00/07680
§ 371 (c)(1),
(2), (4) Date: Mar. 15, 2002

(87) PCT Pub. No.: WO01/19339
PCT Pub. Date: Mar. 22, 2001

(30) Foreign Application Priority Data

Sep. 16, 1999 (GB) .............................. 9921958

(51) Int. Cl.[7] .................... A61K 31/724; A61K 31/606
(52) U.S. Cl. ....................................... 514/58; 514/182
(58) Field of Search ................... 514/58, 182

(56) References Cited

U.S. PATENT DOCUMENTS

| | | | |
|---|---|---|---|
| 4,115,414 A | * 9/1978 | Kristensson et al. | 260/397.5 |
| 4,971,802 A | * 11/1990 | Tarcsay et al. | 424/450 |
| 5,134,127 A | 7/1992 | Stella et al. | 514/58 |
| 5,744,460 A | * 4/1998 | Muller et al. | 514/44 |
| 5,804,568 A | 9/1998 | Rubinfeld | 514/58 |

FOREIGN PATENT DOCUMENTS

| | | |
|---|---|---|
| WO | WO8402270 | 12/1983 |
| WO | 96 09072 | 3/1996 |
| WO | WO9851282 | 5/1998 |

OTHER PUBLICATIONS

Loftsson, T. et al "Estramustine: hydrolysis, solubilization, and stabilization in aqueous solutions" Int. J. Pharm., (1992) vol 79, pp. 107–112.*

Gunnarsson, P., et al "Pharmacokinetics of Estrmustine Phosphate . . . " Eur. J. Clin. Pharmacol., (1984), vol 26, pp. 113–119.*

* cited by examiner

Primary Examiner—James O. Wilson
Assistant Examiner—Leigh C. Maier
(74) Attorney, Agent, or Firm—McDonnell Boehnen Hulbert & Berghoff LLP

(57) ABSTRACT

A pharmaceutical formulation which comprises a parenterally acceptable carrier or diluent, estramustine phosphate and a sulfoalkyl ether cyclodextrin. The formulation can be administered according to a combined chemotherapy regimen in association with one or more chemotherapeutic agents. The formulation also enables estramustin phosphate to be administered with no side effects at the site of injection.

22 Claims, No Drawings

FORMULATIONS FOR PARENTERAL USE OF ESTRAMUSTINE PHOSPHATE AND SULFOALKYL ETHER CYCLODEXTRINS

This application is the National Stage entry of PCT/EP 00/07680, filed Aug. 3, 2000.

The present invention relates to pharmaceutical formulations of estramustine phosphate for parenteral use and, more particularly, to formulations of estramustine phosphate for parenteral use further comprising sulfoalkyl ether cyclodextrins.

Estramustine phosphate (The Merck Index, XII Ed., No. 3749, 1996) is an estradiol-17 β-phosphate derivative widely known in the art as antitumor agent, currently used in the treatment of advanced adenocarcinoma of the prostate.

The drug is usually administered orally, preferably at a dose of 10–15 mg/kg/day. Intravenous administration, however, is also adopted in some particular cases.

For example, initial intravenous administration of estramustine phosphate, followed by oral administration, has been reported at dosages paralleling the oral administration for the drug, i.e. 300–600 mg daily given intravenously and usually repetitively over for several consecutive days (see, for a reference, British Journal of Urology, 1977, 49, 73–79; J. Urol.108:303–306, 1972; Eur. Clin. Pharmacol. 26(1), 113–119, 1984; Eur. Urol. 1990, 17, 216–218).

Estramustine phosphate as well as other well-known cytotoxic compounds used in antitumor therapy are known to cause, or potentially cause, vascular damages at the site of injection when parenterally, in particular intravenously, administered.

As an example, studies in patients treated with estramustine phosphate administered as a slow intravenous injection or as a bolus, at 300 mg/day, revealed thrombophlebitis and local irritations at the peripheral intravenous injection sites.

These drawbacks are considered major limitations for the intravenous administration of estramustine phosphate, thus requiring, in many patients, the establishment of central line administration or, in some cases, even discontinuation of the treatment.

With the aim of minimising the unwanted effects associated with the intravenous administration of cytotoxic agents, a few means are reported in the art.

Among them is the use of hydroxypropyl-cyclodextrin, in the preparation of formulations for parenteral administration of cytotoxic known to cause ulcerative lesions. See, for a reference, U.S. Pat. No. 5,804,568 in the name of Supergen Inc.

Sulfoalkyl ether cyclodextrins are known in the art as solubilizing agents for insoluble or poorly soluble drugs (see, for a reference, U.S. Pat. No. 5,134,127 in the name of the University of Kansas).

In this respect, we found formulations for parenteral use comprising estramustine phosphate together with sulfoalkyl ether cyclodextrins which, unexpectedly, resulted to achieve optimal protection from side-effects associated with estramustine administration.

It is therefore the object of the present invention a formulation for parenteral use comprising estramustine phosphate in admixture with a sulfoalkyl ether cyclodextrin.

Once administered intravenously to patients, the formulations object of the present invention do not provoke ulcerative damages, nor thrombophlebitis, at the site of injection.

In the present invention, unless otherwise specified, with the term formulation comprising estramustine phosphate, as the active ingredient, we intend any formulation comprising estramustine phosphate either in the acid form or as a pharmaceutically acceptable salt for parenteral administration such as, for instance, a salt with a basic amino acid or with N-methyl glucamine, otherwise referred to as meglumine.

Preferably, estramustine phosphate is in the form of its meglumine salt. With the term sulfoalkyl ether cyclodextrin we refer to any cyclodextrin of the above type wherein alkyl stands for straight or branched $C_1$–$C_6$ alkyl group such as methyl, ethyl, n.propyl, isopropyl, n.butyl, isobutyl, sec-butyl, tert-butyl, n.pentyl, n.hexyl and the like.

Preferably, the formulations of the present invention comprise estramustine phosphate in admixture with sulfobutyl ether β-cyclodextrin.

According to a preferred embodiment of the invention, the above formulations are advantageously used for intravenous use.

As such, these formulations of the invention can be administered to patients either as a slow injection, e.g. over about 30 minutes to about 3 hours, or as a bolus injection, also referred to as IV (intravenous) push.

Preferably, these formulations comprise estramustine phosphate in admixture with a sulfoalkyl ether cyclodextrin wherein the weight ratio between estramustine phosphate and sulfoalkyl ether cyclodextrin is from about 1:1 to about 1:5, respectively.

Formulations containing even higher amounts of sulfoalkyl ether cyclodextrin with respect to the active, are however still effective and thus comprised within the scope of the present invention.

In addition, it is herewith provided a very advantageous method for delivering estramustine phosphate intravenously, even when high doses of the active are needed.

It is therefore a further object of the invention a formulation for parenteral use comprising estramustine phosphate, as a single infusion dosage of the active exceeding 1300 mg, in admixture with a sulfoalkyl ether cyclodextrin.

According to another preferred embodiment of the invention, it is further provided a formulation for parenteral use comprising estramustine phosphate, as a single infusion dosage of the active exceeding 950 mg/m$^2$, in admixture with a sulfoalkyl ether cyclodextrin.

In a yet further preferred embodiment, the estramustine phosphate is provided in lyophilised form and the sulfoalkyl ether cyclodextrin is provided in physiological solution. Formulations of this type may typically be presented as a kit.

The formulations object of the present invention allow the administration of the active either as a single agent or, alternatively, in combination with known anticancer treatments such as radiation therapy or chemotherapy regimen in combination with cytostatic or cytotoxic agents, antibiotic-type agents, alkylating agents, antimetabolite agents, hormonal agents, e.g. aromatase inhibitors, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

As an example, the above formulations can be administered in combination with one or more chemotherapeutic agents, optionally within liposomal formulations thereof.

Examples of chemotherapeutic agents are, for instance, taxane, taxane derivatives, CPT-11, camptothecin and derivatives thereof, anthracycline glycosides, e.g. doxorubicin, idarubicin or epirubicin, etoposide, navelbine, vinblastine, carboplatin, cisplatin and the like, optionally within liposomal formulations thereof.

In addition, the above formulations can be also administered in combination with protein kinase inhibitors such as, for instance, the indolinone derivatives disclosed by Sugen in the international patent applications WO 96/40116 and WO 99/61422, which are herewith incorporated by reference.

In this respect, the formulations object of the invention can be preferably administered in combination with 3-[4-(2-carboxyethyl-3,5-dimethylpyrrol-2-yl)methylidenyl]-2-indolinone and 3[(2,4-dimethylpyrrol-5-yl)methylidenyl]-2-indolinone, better known as Sugen SU 6668 and SU 5416, respectively.

The formulations of the invention may be administered sequentially with known anticancer agents when a combination formulation is inappropriate.

Therefore, it is a further object of the present invention a product containing a formulation for parenteral use of estramustine phosphate in admixture with a sulfoalkyl ether cyclodextrin and one or more chemotherapeutic agents, as a combined preparation for simultaneous, separate or sequential use in anticancer therapy.

Toxicology

To study the local irritant effects of estramustine phosphate after repeated intravenous administrations to rats, in comparison to a formulation of estramustine phosphate according to the present invention, the active was dissolved in different vehicles such as water solution for injection and water solution for injection further containing different amounts of sulfoalkyl ether cyclodextrin.

In particular, the following solutions of estramustine phosphate: sulfobutyl ether β-cyclodextrin in a weight ratio of 1:2 and of 1:4, respectively, were prepared and tested.

Male Sprague-Dawley rats were used because of their acceptance as a predictor of toxic change in man. The rats were 6 weeks old at the start of the study.

Estramustine phosphate, in the form of meglumine salt, was administered to groups of rats as a repeated intravenous injection during 3 days. Rats were then sacrificed: a half of the rats at the fourth day and a half at the fifth day. The dose level of estramustine phosphate, in all the different tested solutions, was of 150 mg/kg/day.

Clinical observations were recorded daily. Thrombophlebitic side effects resulted in a dark bluish/blackish coloration of the tail during the treatment period.

A score system based on tail coloration and its extension was used to evaluate the different tested formulations. The score system considered estramustine phosphate water solution as the positive control (i.e. marked toxicity). Water for injection was administered to the control group as negative control (i.e. no toxicity signs).

Histological evaluation was carried out on the tail of the rats treated with the composition of the invention. Estramustine phosphate in a water solution induced, at the used dose, local irritant effects at the injection site after the first administration and marked toxicity signs at the end of the experiment.

Sulfobutyl ether β-cyclodextrin containing formulations, according to the present invention, showed no toxicity signs even when this excipient was present at low concentrations. Histological evaluation of the tail of the rats treated with the formulations containing sulfobutyl ether β-cyclodextrin did not reveal any damage when compared to the tails of the control group.

It was thus concluded that estramustine phosphate in a water solution containing sulfoalkyl ether cyclodextrin, according to the present invention, induced markedly less local irritant effects when compared with a water solution of the same.

One particularly preferred schedule for administering the formulation of estramustine phosphate according to the invention is a single infusion given once weekly to a maximal dose of 4000 mg or 3500 mg/m$^2$.

Another preferred schedule is the administration of a single drug infusion once every two to four weeks. One schedule may be preferred over another in consideration of schedules with other optional concomitant therapy. These schedules may repeat in serial or as repetitive fashion.

The formulations of the present invention are useful in antitumor therapy, particularly in the treatment of prostate cancer, breast cancer, melanoma, lung cancer, pancreatic cancer, colorectal cancer, ovarian cancer and cancers of the brain.

The formulations object of the present invention are prepared according to conventional techniques adopted in the preparation of pharmaceutical forms for parenteral use. Typically, a proper amount of estramustine phosphate, either as a dry powder or into a lyophilised form, is dissolved in a pharmaceutically acceptable solution for parenteral use and then admixed with a proper amount of a sulfoalkyl ether cyclodextrin, for instance sulfobutyl ether β-cyclodextrin.

As an example, a proper amount of estramustine phosphate in the form of a suitable salt such as, for instance, N-methyl glucamine salt, is dissolved in a suitable amount of sterile water or aqueous dextrose solution, e.g. 5% dextrose in water for intravenous administration, and then admixed with a proper amount of powdered sulfobutyl ether β-cyclodextrin.

The above admixture is then stirred, sterilised, and subsequently lyophilised according to conventional techniques.

The freeze-dried formulation is prepared and stored in vials for injection; the addition of a proper amount of sterile water or a physiological solution for parenteral use enables the preparation of the final formulation to be injected.

Alternatively, the final formulation to be injected may be prepared by reconstituting the freeze-dried formulation comprising the active principle with a proper amount of sterile water or of a physiological solution for parenteral use already containing a proper amount of a sulfoalkyl ether cyclodextrin.

The above method is also suitable for preparing high dosages estramustine phosphate formulations whilst maintaining the desired weight ratio between the components.

The unit strength of the formulation to be injected depended on the concentration of the active in the solution itself and, of course, on the filling volume of the vials used to prepare the final formulation.

Additionally, the formulations of the present invention may optionally contain pharmaceutically acceptable excipients for parenteral administration such as, for instance, bulking agents, e.g. lactose or mannitol, pH buffering agents, anti-oxidant agents, preservative agents, tonicity adjusters and the like.

The following examples are herewith intended to better illustrate the present invention without representing any limitation to it.

EXAMPLE 1

Preparation of Estramustine Phosphate:sulfobutyl Ether β-cyclodextrin=1:4.2 Weight Ratio 300 mg of estramustine phosphate were weighed in a beaker and dispersed by means of magnetic stirring in 5 ml of water. 120.8 mg of N-methyl-glucamine were then added under stirring to the watery dispersion of the active and, after a few minutes, a clear solution was obtained. 1250 mg of sulfobutyl ether β-cyclodextrin were added, maintaining the solution under stirring until complete dissolution.

The obtained solution was then brought to the final volume of 10 ml with water so as to reach a final concentration of 30 mg/ml of estramustine phosphate and 125 mg/ml of sulfobutyl ether β-cyclodextrin (1:4.2 weight ratio—1:1 molar ratio respectively).

A solution prepared as previously described, properly sterilized by filtration, was tested for its local vein tolerability in rats.

EXAMPLE 2

The formulation described in Example 1 was also prepared by solubilization of the commercially available Estracyt® freeze-dried formulation containing 300 mg/vial of the active. The reconstitution of the formulation was made using 10 ml of a 125 mg/ml sulfobutyl ether β-cyclodextrin solution so as to obtain a final concentration of 30 mg/ml of estramustine phosphate and 125 mg/ml of cyclodextrin (1:4.2 weight ratio—1:1 molar ratio respectively).

EXAMPLE 3

Preparation of Estramustine Phosphate:sulfobutyl Ether β-cyclodextrin=1:2.1 Weight Ratio 300 mg of estramustine phosphate were weighed in a beaker and dispersed by means of magnetic stirring in 5 ml of water. 120.8 mg of N-methyl-glucamine were then added under stirring to the watery dispersion of the active and, after a few minutes, a clear solution was obtained. 625 mg of sulfobutyl ether β-cyclodextrin were added, maintaining the solution under stirring until complete dissolution.

The obtained solution was then brought to the final volume of 10 ml with water so as to reach a final concentration of 30 mg/ml of estramustine phosphate and 62.5 mg/ml of sulfobutyl ether β-cyclodextrin (1:2.1 weight ratio—1:0.5 molar ratio respectively).

A solution prepared as previously described, properly sterilized by filtration, was tested for its local vein tolerability in rats.

EXAMPLE 4

The formulation described in Example 3 was also prepared by solubilization of the commercially available Estracyt® freeze-dried formulation containing 300 mg/vial of the active. The reconstitution of the formulation was made using 10 ml of a 62.5 mg/ml sulfobutyl ether β-cyclodextrin solution so as to obtain a final concentration of 30 mg/ml of estramustine phosphate and 62.5 mg/ml of cyclodextrin (1:2.1 weight ratio—1:0.5 molar ratio respectively).

What is claimed is:

1. A pharmaceutical formation which comprises a parenterally acceptable carrier or diluent and estramustine phosphate and a sulfoalkyl ether cyclodextrine.

2. A formulation according to claim 1, wherein the weight ratio of estramustine phosphate to the sulfoalkyl ether cyclodextrin is from about 1:1 to about 1:5.

3. A formulation according to claim 1, which is in single infusing doseage from comprising at least 1300 mg of the estramustine phosphate.

4. A formulation according to claim 1, which is in single infusing doseage from comprising at least 950 mg/m$^2$ of the estramustine phosphate.

5. A formulation according to claim 1, wherein the sulfoalkyl ether cyclodextrine is a straight or branched $C_1$–$C_6$ sulfoalkyl cyclodextrine.

6. A formulation according to claim 5, wherein the sulfoalkyl ether cyclodextrin is sulfobutyl ether β-cyclodextrin.

7. A formulation according to claim 1, wherein the estramustine phosphate is in the form of a pharmaceutically acceptable salt for intravenous use.

8. A formulation according to claim 7 wherein the estramustine phosphate is in the form of N-methyl glucamine salt.

9. A formulation according to claim 1 wherein the parenterally acceptable carrier is a physiological solution for parenteral use which contains the sulfoalkyl ether cyclodextrin, and the extramustine phosphate is in lyophilized form.

10. A method for treatment of cancer comprising parenterally administering the formulation of claim 1 to a patient in need thereof, whereby the cancer is treated.

11. A method as claimed in claim 10 wherein the cancer is prostate cancer, breast cancer, melanoma, lung cancer, pancreatic cancer, colorectal cancer, ovarian cancers or cancer of the brain.

12. The method of claim 10, wherein the formulation is intravenously administered.

13. A method of suppressing or reducing side-effects associated with intravenous administration of estramustine phosphate and pharmaceutically acceptable salts thereof comprising administering the formulation of claim 1 to a patient in need thereof, whereby the side-effects are suppressed or reduced.

14. The method according to claim 13 wherein the side effects comprise ulcerative lesions and thrombophlebitis at the site of injection.

15. A product which comprises (i) a pharmaceutical formulation which comprises a parenterally acceptable carrier or diluent, estramustine phosphate and a sulfoalkyl ether cyclodextrin, and (ii) one or more chemotherapeutic agents; as a combined preparation for simultaneous, separate or sequential use in anticancer therapy.

16. A product according to claim 15 wherein the sulfoalkyl ether cyclodextrin is sulfobutyl ether β-cyclodextrin.

17. A product according to claim 15 wherein the chemotherapeutic agent is selected from taxane, taxane derivatives, CPT-11, camptothecin and derivatives thereof, doxorubicin, idarubicin or epirubicin, etoposide, navelbine, vinblastine, carboplatin, cisplatin, SU 6668 and SU 5416.

18. The product of claim 17, wherein the chemotherapeutic agent is encapsulated within liposomes.

19. A method for treatment of cancer comprising parenterally administering the product of claim 15 to a patient, whereby the cancer is treated.

20. The method according to claim 19, wherein the cancer is prostate cancer, breast cancer, melanoma, lung cancer, pancreatic cancer, colorectal cancer, ovarian cancer or cancer of the brain.

21. The method of claim 19, wherein the product is intravenously administered.

22. A product which comprises estramustine phosphate in lyophilized form and a physiological solution for parenteral use containing a sulfoalkyl ether cyclodextrin.

* * * * *